(12) United States Patent
Kriz et al.

(10) Patent No.: US 8,633,014 B2
(45) Date of Patent: Jan. 21, 2014

(54) DEVICE FOR BIOCHEMICAL PROCESSING AND ANALYSIS OF A SAMPLE

(75) Inventors: Dario Kriz, Höör (SE); Kirstin Kriz, Höör (SE)

(73) Assignee: LifeAssays AB (Publ), Lund (SE)

( * ) Notice: Subject to any disclaimer, the term of this patent is extended or adjusted under 35 U.S.C. 154(b) by 731 days.

(21) Appl. No.: 12/734,586

(22) PCT Filed: Oct. 24, 2008

(86) PCT No.: PCT/SE2008/051205
§ 371 (c)(1),
(2), (4) Date: May 11, 2010

(87) PCT Pub. No.: WO2009/064240
PCT Pub. Date: May 22, 2009

(65) Prior Publication Data
US 2011/0104659 A1    May 5, 2011

(30) Foreign Application Priority Data

Nov. 13, 2007    (SE) ...................................... 0702496

(51) Int. Cl.
*C12M 1/34*    (2006.01)
(52) U.S. Cl.
USPC .................................................... 435/287.2
(58) Field of Classification Search
None
See application file for complete search history.

(56) References Cited

U.S. PATENT DOCUMENTS

| | | | |
|---|---|---|---|
| 3,188,468 A | | 6/1965 | Packard |
| 5,252,493 A | * | 10/1993 | Fujiwara et al. ............. 436/526 |
| 5,528,142 A | | 6/1996 | Feickert |
| 5,906,795 A | | 5/1999 | Nakashima et al. |
| 6,110,660 A | | 8/2000 | Kriz et al. |
| 7,718,135 B2 | * | 5/2010 | Himmelsbach et al. ...... 422/527 |
| 8,295,741 B2 | * | 10/2012 | Kido ............................ 399/260 |
| 2001/0050555 A1 | | 12/2001 | Hawkins et al. |
| 2003/0020463 A1 | * | 1/2003 | Carlson et al. ................ 324/204 |
| 2005/0093535 A1 | | 5/2005 | Kriz |
| 2006/0091885 A1 | * | 5/2006 | Rindlisbacher et al. ...... 324/321 |
| 2007/0202017 A1 | * | 8/2007 | Himmelsbach et al. ...... 422/102 |

FOREIGN PATENT DOCUMENTS

| | | |
|---|---|---|
| EP | 1 146 347 | 10/2001 |
| EP | 1146347 | * 10/2001 |
| SE | 9502902 | 6/2003 |
| SE | 524 168 | 7/2004 |

OTHER PUBLICATIONS

Kriz, C., et al., "Magnetic Permeability Measurements in Bioanalysis and Biosensors," Analytical Chemistry, vol. 68, No. 11, pp. 1966-1970, Jun. 1, 1996.
Spraul, M., et al., "Evaluation of Liquid Chromatography Coupled with High-Field $^1$H NMR Spectroscopy for Drug Metabolite Detection and Characterization:the Identification of Paracetamol Metabolites in Urine and Bile," NMR in Biomedicine, vol. 7, pp. 295-303, 1994.
Kriz, K., et al., "Advancements toward magneto immunoassays," Biosensors & Bioelectronics, vol. 13, pp. 817-823, 1998.
Hawkins, P., et al., "Measuring system for the rapid determination of the concentration of coated micrometer-sized paramagnetic particles suspended in aqueous buffer solutions," Review of Scientific Instruments, vol. 72, No. 1, pp. 237-242, Jan. 2001.
Larsson, K. et al., "Magnetic Transducers in Biosensors and Bioassays," Analusis, vol. 27, No. 7, pp. 617-621, 1999.
SE 520 150 Abstract published Jun. 3, 2003.

* cited by examiner

*Primary Examiner* — Ann Lam
(74) *Attorney, Agent, or Firm* — Harness, Dickey & Pierce P.L.C.

(57) ABSTRACT

A device including a sample compartment, a coil and an arm for mechanical manipulation of a sample vessel placed in the sample compartment and containing a sample is described. In at least one embodiment, the coil is surrounding the sample compartment and the sample compartment has an opening for insertion and removal of the sample vessel. A method, using the device according to at least one embodiment of the invention for detection of magnetic permeability, relative magnetic permeability or relative magnetic susceptibility, is also described.

19 Claims, 1 Drawing Sheet

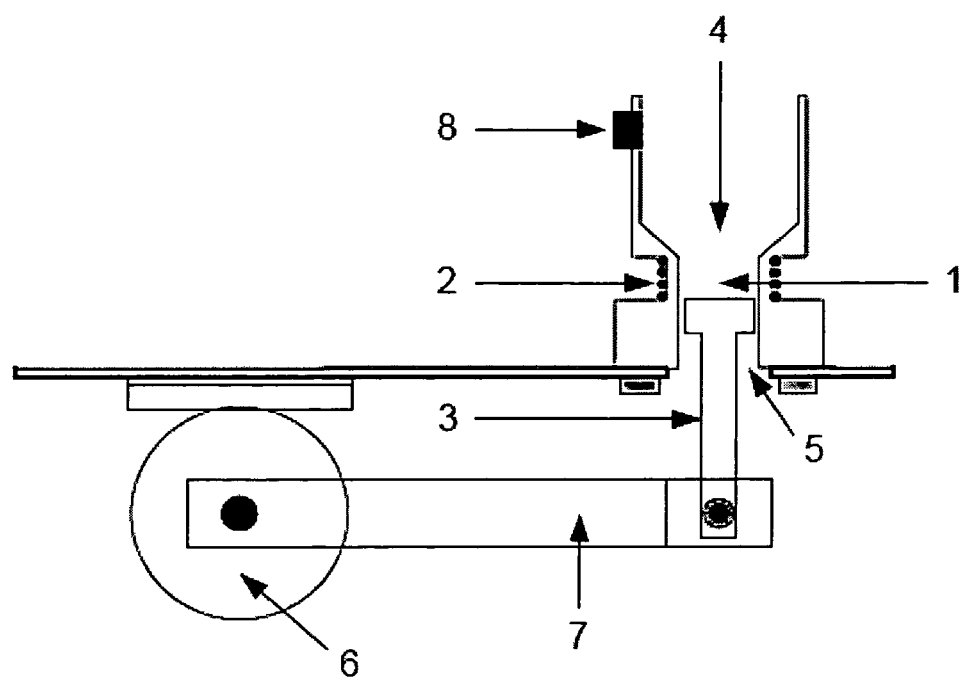

DEVICE FOR BIOCHEMICAL PROCESSING AND ANALYSIS OF A SAMPLE

TECHNICAL FIELD

The present invention relates to a device to be used for measuring magnetic permeability ($\mu$) or alternatively relative magnetic permeability ($\mu_r$).

BACKGROUND ART

The annual world market for diagnostic equipment based on immunoassays has grown greatly over the past decades. The main reason for the success of immunoassays is that the method is general and easy to adjust to various chemical analytical problems. The use of different types of detection technologies in combination with immunoassays has made it possible to identify and quantify a number of important chemical substances. Depending on the physical measuring principle, different types of detectors are suited for different types of analytical problems. After the introduction of immunoassays, several detectors have been presented and exhibited excellent performance data. One type of detector uses magnetic permeability as a basis for detection. Such a detector, which is described in SE9502902-1 and U.S. Pat. No. 6,110,660, enables quick and easy identification of substances using immunoassay technology. The measurements are performed by samples being placed in a special measuring coil whose inductance is measured and compared with a separate air-filled reference coil. This type of device enables measuring of magnetic permeability in samples, however with the drawback that the temperature-dependent drift limits the susceptibility of the detector. The temperature drift is caused by variations in the temperature of the sample and by the temperature of the measuring and reference coils being differently affected by the actual measuring process.

The present invention solves in a new and effective manner the problem with temperature-dependent drift in measuring magnetic permeability or alternatively relative magnetic permeability. Moreover it is possible to obtain measuring data that are based on average values of several automatic measurements in succession, which increases performance compared to prior art technique.

Other prior art techniques comprise a device based on a sample compartment with an integrated double coil according to SE524168. The device does not, however, comprise an arm by which the sample vessel in an automated manner can be mechanically manipulated for increased performance. In addition, the device is based on the use of two coils whose temperature is changed similarly and whose properties therefore must be matched (harmonised). The present invention is based on a coil whose properties are changed when inserting and removing the sample vessel, the temperature of the coil being kept constant.

Magnetoimmunoassays are based on the principle that a sample vessel, containing one or more magnetic reagents, and a liquid, is supplied with a sample and placed in an instrument for reading the concentration of an analyte. (Kriz et al., Analytical Chemistry 68, p1966 (1996); Kriz et al., Biosensors & Bioelectronics 13, p817 (1998); Larsson K. et al. Analusis 27, p78, 1999).

The above-mentioned documents, SE9502902-1, U.S. Pat. No. 6,110,660, SE524168, and Larsson K. et al. Analusis 27, p78, 1999, describe prior art devices and methods, which use detection of magnetic permeability for quantitative chemical analyses in samples placed in a measuring coil. Said devices and methods do not, however, comprise a movable coil mechanism based on a device for measuring of sample vessels.

Other prior art techniques also comprise a flow detector for liquid chromatography, which is based on measuring of NMR, Nuclear Magnetic Resonance (Spraul M. et al. NMR Biomed 7, 295-303, 1994). This detector does not, however, measure magnetic permeability, which is a macroscopic property with its origin outside the atomic nucleus in a material, contrary to NMR. In addition, this device does not comprise a movable coil mechanism according to the present invention.

SUMMARY OF THE INVENTION

The present invention thus relates to a device, characterised in that it comprises a sample compartment (1) which is surrounded by a coil (2), the coil (2) being connected to an electric measuring circuit which measures the inductance of the coil, and the device further being characterised in that it comprises an arm (3) for mechanical manipulation of a sample vessel placed in said sample compartment (1) and containing a sample, and said sample compartment (1) having an opening (4) for insertion and removal of said sample vessel.

By the mechanical manipulation, a sample vessel is moved into and out of the coil, which means that the inductance of the coil is affected momentarily. Since the temperature change of the coil which is caused by the sample vessel and instrument drift is a slow process with a time constant of 10-100 s, the influence of the temperature drift on the measurement of the inductance of the coil can be eliminated by the values of measured inductance before and after the insertion of the sample vessel being subtracted. The device may advantageously be automated by introduction of a microprocessor with software controlling the mechanical manipulation and calculating the obtained inductance differences, said microprocessor being capable of calculating the average of a plurality of measurements on one and the same sample vessel, which increases the accuracy of the measurement. The device can qualitatively and quantitatively analyse the contents of chemical substances in a sample vessel placed in said sample compartment.

The invention also relates to a method in which a device according to the invention is used for qualitative and respectively quantitative analysis of glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus A, Heliobacter Pylori, Salmonella, Chlamydia, Giardia, cholera*, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, in various types of industrial process control, quality control, research and laboratory work.

BRIEF DESCRIPTION OF THE DRAWING

FIG. 1 shows the device according to the present invention, (cut through the centre of the sample compartment (1)) with a sample compartment (1), a coil (2) and an arm (3) for mechanical manipulation of a sample vessel placed in the sample compartment (1) and containing a sample, said coil (2) surrounding said sample compartment (1) and said sample compartment (1) having an opening (4) for insertion and removal of said sample vessel.

DETAILED DESCRIPTION OF THE INVENTION

According to one aspect of the invention, the device is characterised in that said sample compartment (1) has a second opening (5) for insertion of said arm (3) and that the inserted arm (3) has the form of a plunger which can be moved back and forth in said sample compartment (1) and thereby mechanically move said sample vessel when it is placed in the sample compartment (1).

According to a further aspect, the device is characterised in that the arm (3) is made of a material with a relative magnetic permeability in the range of $0.999<\mu_r<1.001$, which gives the advantage that the arm does not magnetically interfere with coil measurements. Examples of such materials are a polymer such as Delrin, POM, polyvinylchloride, Teflon, polyamide, polyacetal, polyethylene, polycarbonate, polystyrene, polypropylene, wood, glass or metal.

According to another aspect, the device is characterised in that said arm (3) has the form of a cylinder which surrounds the outside of said sample compartment (1), and that said arm (3) can be moved back and forth along said sample compartment (1) and thereby mechanically move said sample vessel when it is placed in the sample compartment (1), via a collar projecting from the sample vessel or a recess.

According to one aspect of the invention, the device is characterised in that said arm (3) has the form of a cylinder, or a tube, or a rod, or a wire, or a bar which from above holds the cap of said sample vessel and which can move said sample vessel back and forth and thereby mechanically move said sample vessel in said sample compartment (1). Said cap can be a plug or a projecting collar or a recess of the sample vessel.

According to a further aspect, the device is characterised in that said arm (3) only presses said sample vessel out of said sample compartment (1) and that the return of said sample vessel occurs by gravity, or alternatively that said return occurs by a force exerted by a spring. The spring can be of the type pressure spring or tension spring. The spring can also be connected to the arm (3) or the joint (7) to affect the movement thereof.

According to yet another aspect, the device is characterised in that the movement of said arm (3) is controlled by a reversible motor (6), to which the arm is attached directly or via a joint (7), the reversible motor (6) being controllable by software in a microprocessor or by an independent digital or analogue control electronics circuit. In an alternative embodiment, the motor is replaced by a non-reversible motor and the return movement is produced by gravitational movement (due to the weight of the arm or the sample vessel) or by stored energy in a pressure or tension spring. In a further alternative embodiment, the motor is replaced by an electromagnet.

According to one aspect of the invention, the device is characterised in that it is provided with a microprocessor-controlled electronic measuring circuit, which automatically measures changes in the inductance of said coil (2) that arise in said mechanical movement of said sample vessel in said sample compartment (1). The design of the electronic measuring circuit can be made in various ways by a person skilled in the art and falls beyond this application. Some of these designs are based on alternating current bridges and are described in the references stated in the present application. Well established standard connections for microprocessors (such as PIC 16F876) are available, in which the internal analogue to digital (AD) converter of the microprocessor can be connected to the electronic measuring circuit for collection of measured inductance value, one or more of the output pins of the microprocessor (for instance output B0 and B1 according to data sheets for PIC 16F876 established by the manufacturer Microchip, USA).

A great selection of microprocessors from various manufacturers are commercially available.

According to one aspect of the invention, the device is characterised in that it comprises an optical bar code reader (8), by which a bar code placed on the sample vessel can be automatically read through said mechanical movement. As bar code readers, use can be made of commercially available optical readers of a one and two-dimensional type. Since the sample vessel is moved linearly, the detector of a fixed, non-scanning optics can be used to read a bar code or some other type of light-interacting marking. A bar code or some other type of light-interacting marking is used on the sample vessel to ensure and guarantee the quality of measurements in nursing and industry.

According to one aspect of the invention, the device is characterised in that said coil (2) has, when filled with air, an inductance in the range 0.01 µH to 10 mH, that said sample compartment (1) has a compartment volume in the range 0.1 to 5000 µl, and that the material of which the sample compartment (1) is made is a polymer, such as Delrin, POM, polyvinylchloride, Teflon, polyamide, polyacetal, polyethylene, polycarbonate, polystyrene, polypropylene, wood, glass or metal with $0.999<\mu_r<1.001$.

According to yet another aspect, the device is characterised in that it is provided with an electronic circuit whose output signal is proportional to the inductance of the coil (2) and to the relative magnetic permeability ($\mu_r$) of the sample (solution or suspension or sediment layer) supplied to the sample compartment, in the range $0.9<\mu_r<10$.

According to a further aspect, the device is characterised in that it is provided with two or more identical coil mechanism designs according to the present application for simultaneous detection of a plurality of sample vessels.

According to another aspect, the device according to the invention is characterised in that it is provided with supplementary prior art physical measuring technologies for determining light absorbance, light emission, dissolved gas, ion content and electric conductivity.

The device according to the invention may advantageously be used for detection of magnetic permeability µ or alternatively relative magnetic permeability $\mu_r$ (in the range $0.9<\mu_r<10$) or alternatively relative magnetic susceptibility ($\mu_r-1$) of various chemical substances placed in said sample vessel.

The device according to the invention may advantageously be used for said mechanical movement to be made more than once for each sample vessel for the purpose of allowing said microprocessor to calculate an average value and/or standard deviation related to the changes in the inductance of said coil which arise in said mechanical movement, said changes being proportional to the relative magnetic permeability of said sample in said sample vessel.

It is obvious to a person skilled in the art that the indications of measurements given in FIG. 1 can easily be varied by a factor 10 up and down without the spirit of the invention being changed. Furthermore the relationship of the various measurements in the FIGURE can be changed without the basic principle of the function being changed. All such modifications are considered to fall within the present invention.

The device according to the invention may advantageously be used for said mechanical movement to be used to communicate in different ways with the user by said sample vessel being kept permanently pressed out of the sample compartment (1) to indicate a completed measurement to the user, said sample vessel again placed in said sample compartment (1) being an indication to the device from the user that a new measurement is to be begun, said sample vessel subjected to said mechanical movement indicating to the user that the instrument is occupied by a measurement, checking for how long the user handles said sample vessel when removed from the sample compartment (1) before return thereof in order to signal whether a measurement is disturbed by too long handling.

The device according to the invention may advantageously be used for detection of chemical substances whose $\mu_r>1$.

The device according to the invention may advantageously be used, by interaction with magnetic markers, for qualitative and respectively quantitative near patient analysis of glucose, C-reactive protein (CRP and hsCRP), albumin, cystatin C, hemoglobin (Hb and HbA1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus A, Heliobacter Pylori, Salmonella, Chlamydia, Giardia, cholera*, Hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, in various types of body fluids such as blood, plasma, urine, sweat, tears, lymph, cerebrospinal fluid and faeces.

The device according to the invention may, irrespective of purpose, advantageously be used, under circumstances with a varying sample vessel temperature, to eliminate or greatly minimise the effect of the temperature-caused drift.

FIG. 1 illustrates the device according to the present invention (scale 1:1). The device according to FIG. 1 comprises a sample compartment (1) of Delrin plastic, a coil (2) which consists of 50 loops of wound copper wire (enamelled) with the diameter 0.2 mm and an arm (3) of Delrin plastic for mechanical manipulation of a sample vessel placed in said sample compartment (1) and containing a sample, said coil (2) surrounding said sample compartment (1) and said sample compartment (1) having an opening (4) for insertion and removal of said sample vessel. The sample compartment (1) has a second opening (5) for insertion of said arm (3), and the inserted arm (3) has the form of a plunger which can be moved back and forth in the sample compartment (1) and thereby mechanically move said sample vessel when it is placed in the sample compartment (1). The arm (3) is connected to a joint (7) of Delrin plastic which is attached to a 6 volt downshifted (43:1, 52 rpm) to reversible direct current motor.

The invention claimed is:

1. A device, comprising:
    a sample compartment;
    a coil;
    an arm for mechanical manipulation of a sample vessel placed in said sample compartment and containing a sample; and
    an optical bar code reader, by which a bar code placed on the sample vessel is automatically readable through the mechanical manipulation, said coil surrounding said sample compartment and said sample compartment including an opening for insertion and removal of the sample vessel.

2. A device as claimed in claim 1, wherein the arm is made of a material with a relative magnetic permeability in the range of $0.999<\mu_r<1.001$.

3. A device as claimed in claim 1, wherein said sample compartment includes a second opening for insertion of said arm and wherein said arm when inserted, is in form of a plunger which is movable back and forth in said sample compartment to thereby mechanically move the sample vessel when the sample vessel is placed in the sample compartment.

4. A device as claimed in claim 1, wherein said arm is in form of a cylinder which surrounds the outside of said sample compartment, and wherein said arm is movable back and forth along said sample compartment to thereby mechanically move the sample vessel when the sample vessel is placed in the sample compartment, via a collar projecting from the sample vessel or a recess.

5. A device as claimed in claim 1, wherein said arm is in form of at least one of a cylinder, a tube, a rod, a wire, and a bar which, from above, holds the cap of the sample vessel and which is able to move the sample vessel back and forth to thereby mechanically move the sample vessel in said sample compartment.

6. A device as claimed in claim 1, wherein said arm only presses the sample vessel out of said sample compartment and wherein the return of the sample vessel occurs by at least one of gravity and a force exerted by a spring.

7. A device as claimed in claim 3, wherein the movement of said arm is controlled by a reversible motor, to which the arm is attached directly or via a joint, the reversible motor being controllable by software in at least one of a microprocessor, an independent digital, and an analogue control electronics circuit.

8. A device as claimed in claim 1, further comprising:
    a microprocessor-controlled electronic measuring circuit, to automatically measure changes in inductance of said coil that arise in the mechanical manipulation of the sample vessel in said sample compartment.

9. A device as claimed in claim 1, wherein said coil includes, when filled with air, an inductance in the range 0.01 µH to 10 mH, the sample compartment includes a compartment volume in the range 0.1 to 5000 µl, and a material of the sample compartment is made from a polymer of at least one of polyoxymethylene, polyvinylchloride, polytetrafluorethylene, polyamide, polyacetal, polyethylene, polycarbonate, polystyrene, polypropylene, wood, glass, and metal with $0.999<\mu_r<1.001$.

10. A method, comprising:
    using the device as claimed in claim 1 for detection of at least one of magnetic permeability $\mu$, relative magnetic permeability $\mu_r$ in the range $0.9<\mu_r<10$ and relative magnetic susceptibility $(\mu_r-1)$ of various chemical substances placed in the sample vessel.

11. A method, comprising:
    using the device as claimed in claim 8, wherein the mechanical manipulation is carried out more than once for each sample vessel in order for the microprocessor to be able to calculate at least one of an average value and standard deviation related to the changes in inductance of said coil which arise in the mechanical manipulation, the changes being proportional to the relative magnetic permeability of said sample in the sample vessel.

12. A method, comprising:

using the device as claimed in claim 1, wherein the mechanical manipulation is used to communicate in different ways with the user by said sample vessel being kept permanently pressed out of the sample compartment to indicate a completed measurement to the user, said sample vessel again placed in said sample compartment being an indication to the device from the user that a new measurement is to be begun, said sample vessel subjected to said mechanical manipulation indicating to the user that the instrument is occupied by a measurement, and checking, by the user, how long the user handles said sample vessel when removed from the sample compartment before return thereof in order to signal whether a measurement is disturbed by a long period of handling.

13. A method, comprising:

using the device as claimed in claim 1 for detection of chemical substances whose $\mu_r > 1$.

14. A method, comprising:

using the device as claimed in claim 1, by interaction with magnetic markers, for qualitatiVe and respectively quantitative near patient analysis of glucose, C-reactive protein (CRP and hsCRP), albumin, cystatin C, hemoglobin (Hb and HbA 1C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus A, Heliobacter Pylori, Salmonella, Chlamydia, Giardia, cholera*, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, in various types of body fluids such as blood, plasma, urine, sweat, tears, lymph, cerebrospinal fluid and faeces.

15. A method, comprising:

using the device as claimed in claim 1, by interaction with magnetic markers, for qualitative and respectively quantitative analysis of glucose, C-reactive protein (CRP and hsCRP), albumin, cystatin C, hemoglobin (Hb and HbA 1 C), myoglobin, troponin (I and T), CK-MB, creatine kinase (CK), d-dimer, BNP, proBNP, NT-proBNP, prothrombin, APTT, HCG, LH, FSH, PSA, TSH, T3, T4, AFP, CEA, lipoproteins (LDL and HDL), triglycerides, cholesterol, antibodies, *Streptococcus A, Heliobacter Pylori, Salmonella, Chlamydia, Giardia, cholera*, hepatitis (A, B and C) adenoviruses, rotaviruses, proteins, hormones, complementary factors, blood coagulation factors, cell-ligand interactions, cell-cell interactions, platelet aggregations, bacteria, cells, viruses, fungi, yeast, spores, phages, cells, cell organelles, DNA, RNA, in various types of industrial process control, quality control, research and laboratory work.

16. A device as claimed in claim 2, wherein said sample compartment includes a second opening for insertion of said arm and wherein said arm when inserted, is in form of a plunger which is movable back and forth in said sample compartment to thereby mechanically move the sample vessel when the sample vessel is placed in the sample compartment.

17. A device as claimed in claim 2, wherein said arm is in form of a cylinder which surrounds the outside of said sample compartment, and wherein said arm is movable back and forth along said sample compartment to thereby mechanically move the sample vessel when the sample vessel is placed in the sample compartment, via a collar projecting from the sample vessel or a recess.

18. A device as claimed in claim 4, wherein the movement of said arm is controlled by a reversible motor, to which the arm is attached directly or via a joint, the reversible motor being controllable by software in at least one of a microprocessor, an independent digital, and an analogue control electronics circuit.

19. A device as claimed in claim 5, wherein the movement of said arm is controlled by a reversible motor, to which the arm is attached directly or via a joint, the reversible motor being controllable by software in at least one of a microprocessor, an independent digital, and an analogue control electronics circuit.

* * * * *